(12) United States Patent
Bush et al.

(10) Patent No.: US 7,813,879 B2
(45) Date of Patent: Oct. 12, 2010

(54) SYSTEM AND METHOD FOR PROCESSING AND REPORTING BIOLOGICALLY SIGNIFICANT EVENTS

(75) Inventors: Aaron M. Bush, Kearney, MO (US); Jody L. Gosch, Liberty, MO (US); Mark A. Hoffman, Lees Summit, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 732 days.

(21) Appl. No.: 10/911,713

(22) Filed: Aug. 5, 2004

(65) Prior Publication Data

US 2006/0031018 A1    Feb. 9, 2006

(51) Int. Cl.
*G01N 33/48* (2006.01)
(52) U.S. Cl. ....................................................... 702/19
(58) Field of Classification Search .................... 702/19
See application file for complete search history.

(56) References Cited

U.S. PATENT DOCUMENTS

2002/0193967 A1* 12/2002 Siegel ......................... 702/187

* cited by examiner

*Primary Examiner*—Jerry Lin
(74) *Attorney, Agent, or Firm*—Shook, Hardy & Bacon L.L.P.

(57) ABSTRACT

A system and method are provided for processing reports of biological events in order to filter the reports and output the reports to appropriate institutions and individuals for reporting. The system includes a primary filter for receiving a record, evaluating an event contained within the record, identifying any potential receiving organization based on the event evaluation, and creating a record for each potential receiving organization. The system may also include additional filters such as secondary filters, location filters, and column level filters for limiting the records created by the primary filter based on definitions provided by the receiving institutions.

19 Claims, 6 Drawing Sheets

SYSTEM AND METHOD FOR PROCESSING AND REPORTING BIOLOGICALLY SIGNIFICANT EVENTS

CROSS-REFERENCE TO RELATED APPLICATIONS

None.

STATEMENT REGARDING FEDERALLY SPONSORED RESEARCH OR DEVELOPMENT

None.

TECHNICAL FIELD

Embodiments of the present invention relate to reporting of biologically significant events and more particularly to filtering of biological events in order to properly determine appropriate events for reporting to multiple receiving organizations.

BACKGROUND OF THE INVENTION

Due to health and safety concerns, it is often desirable to report certain classes of events from health care institutions to health departments or other organizations. Reportable events may include individual test results, environmental events, and clinical events. Whether or not the biological events are reportable depends upon the preferences of the entity requesting a report.

Health departments or other organizations in different jurisdictions may be concerned with different types of health care events. For instance, some jurisdictions may consider a streptococcal pneumonia diagnosis as reportable and others may not. Likewise, some jurisdictions may consider certain types of poisoning events as reportable and other jurisdictions may not be interested in the same events. Furthermore, jurisdictions are often concerned only with diagnoses of patients living in certain areas and/or with tests conducted in hospitals in specific geographic regions. Currently available reporting systems are unable to handle demands of multiple organizations in multiple jurisdictions. Accordingly, existing reporting systems operate within a single jurisdiction.

Furthermore, even within a jurisdiction, different clinical events may be of interest to different groups and individuals due to overlapping jurisdictional regions or internal departmental organization. For example, while a group of individuals associated with a particular health department may be concerned with a broad range of types of clinical events, specialists within the organization may be focused on specific types of reportable events.

In addition, different users may have different privileges regarding the information elements they are allowed to see. For example, an individual may be allowed to see only the number of results for particular conditions for trending purposes and not any person identifiable information such as name or address. Other individuals may need to see these elements for follow-up or further reporting purposes.

A cohesive system is needed that allows for determination of reportable events to multiple jurisdictions with varying requirements. A system is also needed that will report appropriate events to requesting groups and to requesting individuals within each group. Such a system should appropriately limit the number of reportable events so that no receiving entity receives a large amount of irrelevant data. The system should also allow restrictions to be placed on individual fields so that selected pieces of information will be masked for certain users.

BRIEF SUMMARY OF THE INVENTION

Embodiments of the present invention are directed to a system for processing a biological event record from at least one reporting organization in order to selectively deliver information from the biological event record to at least one receiving organization. The system includes a primary filter for identifying a biological event contained within the biological event record and identifying any potential receiving organization based on the identity of the biological event. The primary filter additionally creates a record for each potential receiving organization. The system also includes an additional filter for evaluating each record created by the primary filter based on definitions provided by the receiving organization for the evaluated record.

In an additional aspect of the invention a system is provided for processing a biological event record from at least one reporting organization in order to deliver information from the biological event record to at least one receiving organization. The system includes a primary filter for receiving the biological event record, evaluating an event contained within the biological event record, identifying any potential receiving organization based on the event evaluation, and creating a record for each potential receiving organization. The system additionally includes a location filter for identifying demographic information of a reporting organization in each created record and comparing the identified demographic information to demographic criteria of the potential receiving organization and deleting the record if the demographic information of the reporting organization does not fall within the demographic criteria of the receiving organization.

In yet a further aspect of the invention, a method is provided for processing a biological event record received from at least one reporting organization and delivering information from the biological event record to at least one receiving organization. The method includes determining if at least one receiving organization has requested notification of the biological event contained within the biological event record and creating a record using a primary filter for each receiving organization that has requested notification of the biological event. The method further includes filtering each record created by the primary filter using an additional filter constructed based on criteria provided by each receiving organization.

In yet an additional aspect, a method is provided for reporting significant biological events reported by a first set of institutions to a second set of receiving institutions. The method includes identifying each receiving institution interested in the biological event and creating a record for each interested receiving institution. The method additionally includes applying a filter to each created record. The filter contains definitions supplied by the interested receiving institution. The method additionally includes determining if the created record satisfies the filter definitions and eliminating the created record if it fails to satisfy the filter definitions. The method further includes reporting the created record to the interested receiving institution if the record satisfies the filter definitions.

In yet an additional aspect of the invention, a system is provided for processing a biological event record from at least one reporting organization in order to selectively deliver information from the biological event record to at least one receiving organization and at least one receiving individual within the at least one receiving organization. The system includes a primary filter for identifying a biological event contained within the biological event record and identifying any receiving organization during a first processing phase and any receiving individual within the receiving organization during a second processing phase. The primary filter creates a record for each receiving organization during the first processing phase and each receiving individual during the second processing phase. The system additionally includes at least one additional filter for evaluating each record created by the primary filter during the first processing phase and the second processing phase to determine event information for passing to each receiving organization during the first processing phase and event information for passing to each receiving individual during the second processing phase.

BRIEF DESCRIPTION OF THE DRAWINGS

The present invention is described in detail below with reference to the attached drawings figures, wherein.

DETAILED DESCRIPTION OF THE INVENTION

I. System Overview

Figure 1:
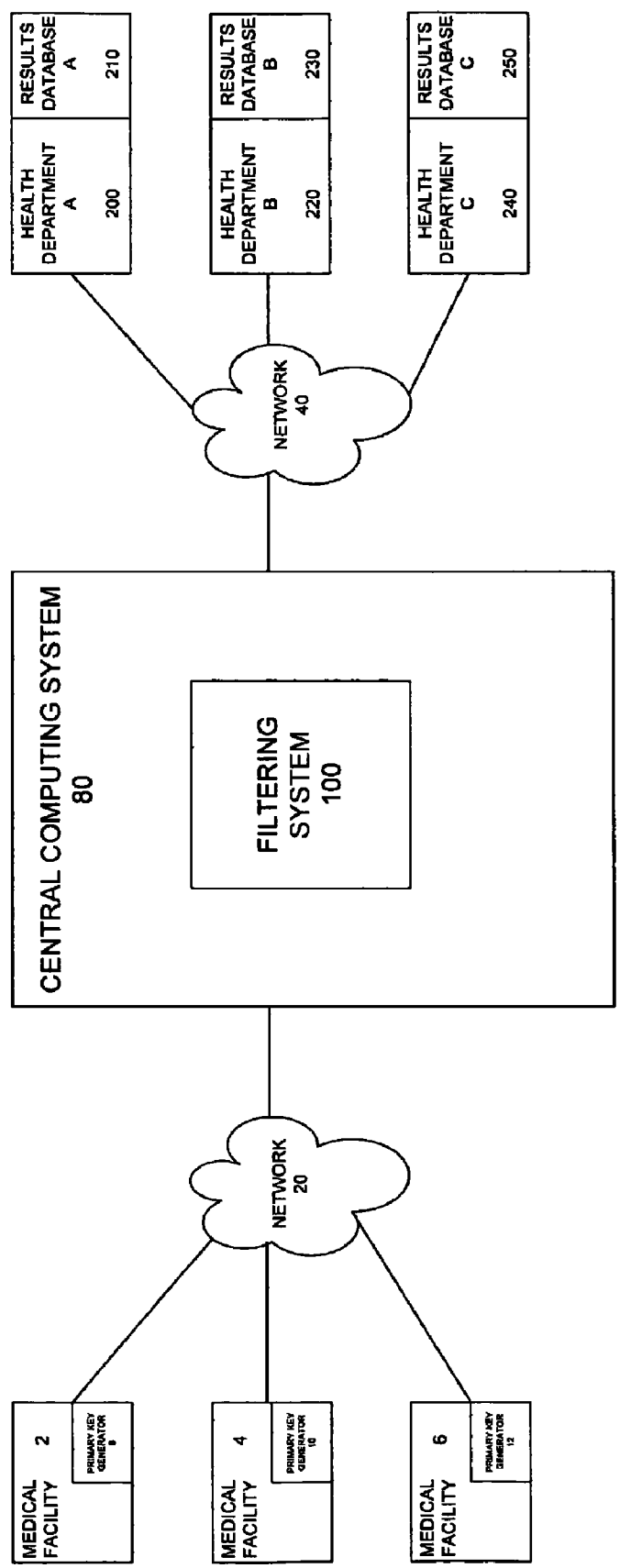
FIG. 1 is a block diagram illustrating an overview of a system in accordance with an embodiment of the invention.

Embodiments of the invention include a method and system for processing biological events to identify and deliver reportable events to appropriate entities. FIG. 1 illustrates a system for receiving and transferring information between a plurality of medical facilities 2, 4, and 6, and multiple health departments 200, 220, and 240. Each medical facility has a primary key generator 8, 10, 12, for sending records over a network 20 to a central computing system 80. The primary key generators 8, 10, 12 are associated with clinical and billing activity (CBA) of a health care institution or medical facility 2, 4, 6. The primary key information produced through CBA typically includes demographic information concerning the patient, facility information, and event information. The demographic information related to the patient may include such information as patient name, patient social security number and patient residence. The facility information preferably includes facility location information such as city, state, and zip code. The event information includes information pertaining to the biological event such as pathogen type and site of pathogen within the patient.

The central computing system 80 includes a filtering system 100 for filtering the received records and outputting received results over a network 40 to results databases 210, 230, and 250 associated with each health department 200, 220, and 240. The networks 20 and 40 may be the same or different networks and may be of any type as described below with reference to the computing system environment.

Figure 2:
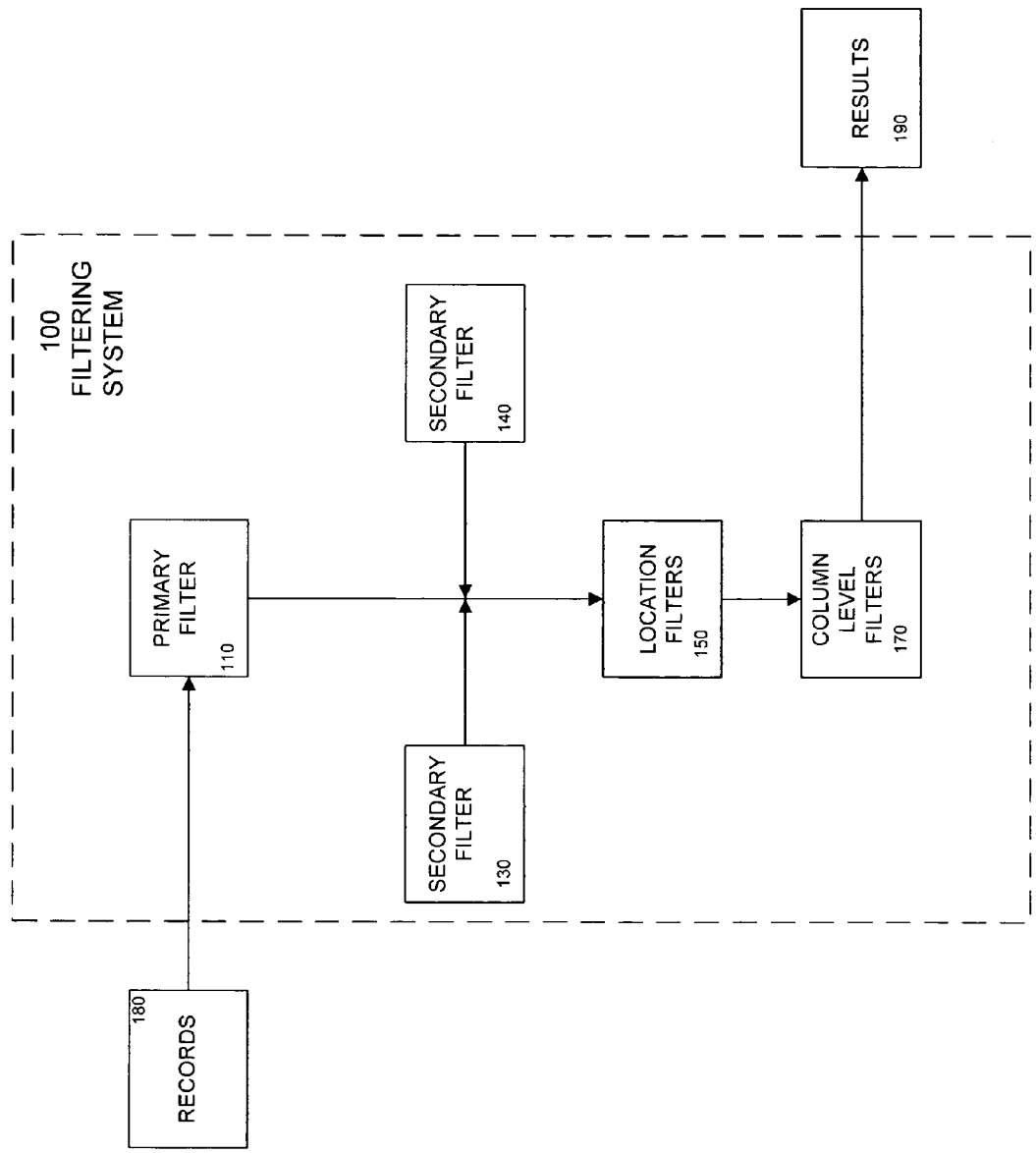
FIG. 2 is a block diagram illustrating components of a filtering system in accordance with an embodiment of the invention.

FIG. 2 illustrates a filtering system 100 in accordance with an embodiment of the invention. The filtering system processes records 180 using a primary filter 110, secondary filters 130, 140, location filters 150, and column level filters 170 to output results 190. As set forth above, a primary key generator 8, 10, 12 associated with each medical facility 2, 4, 6 delivers information in the form of records 180 identifying a biological event to the filtering system 100 within the central computing system 80. The filtering system 100 processes information received from the primary key generators and ultimately delivers results 190 to appropriate results databases 210, 230, 250. As shown, the results databases 210, 230, 250 may be located in multiple locations and multiple organizations. The filtering system 100 ensures that appropriately filtered results are delivered to each distinct results database.

The primary filter 110 processes incoming records to identify an event. Based on information received from the primary key generators 8, 10, 12, the primary filter 110 applies a list of reportable events from multiple jurisdictions. The list of reportable events may be stored within a database attached to or contained within the primary filter 110. If the event listed on the record is not reportable in any subscribing jurisdiction, then the primary filter 110 excludes the record. However, if an event is reportable in any jurisdiction on record, then the primary filter 110 recognizes the event information from the primary key and creates a record for passage to the next filter in the sequence. The primary filter 110 creates a record for each receiving institution interested in the particular event. The primary filter 110 passes the included records to secondary filters 130, 140. The secondary filters 130, 140 filter the created records based on criteria supplied by each organization as will be further explained below and pass included records to the location filters 150 and subsequently to column level filters 170. The location filters 150 filter out records based on patient characteristics and/or characteristics of the reporting or diagnosing institution and the column level filters 170 mask certain fields based on criteria provided by each receiving organization. The remaining records are sent out from the filtering system 100 as results 190 and are directed to the appropriate results database as indicated by the requesting organization.

II. Operating Environment

The filtering system and method may be implemented in a suitable computing system environment associated with the central computing system 80. The invention is described in the general context of computer-executable instructions, such as program modules, being executed by a computer. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote computer storage media including memory storage devices.

An exemplary system for implementing the invention includes a general purpose-computing device including a processing unit, a system memory, and a system bus that couples various system components including the system memory to the processing unit. The computing device typically includes a variety of computer readable media. By way of example, and not limitation, computer readable media may comprise computer storage media and communication media.

The system memory includes computer storage media in the form of volatile and/or nonvolatile memory such as read only memory (ROM) and random access memory (RAM). A basic input/output system (BIOS), containing the basic routines that help to transfer information between elements within computer, such as during start-up, is typically stored in ROM. RAM typically contains data and/or program modules that are immediately accessible to and/or presently being operated on by processing unit.

The computing device may also include other removable/nonremovable, volatile/nonvolatile computer storage media. A hard disk drive may read from or write to nonremovable, nonvolatile magnetic media, a magnetic disk drive that reads from or writes to a removable, nonvolatile magnetic disk, and an optical disk drive may read from or writes to a removable, nonvolatile optical disk such as a CD ROM or other optical media. Other removable/nonremovable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive may typically be connected to the system bus through a non-removable memory interface. The magnetic disk drive and optical disk drive are typically connected to the system bus by a removable memory interface.

A user may enter commands and information into the computing device through input devices such as a keyboard and pointing device, commonly referred to as a mouse, trackball or touch pad. Other input devices may include a microphone, joystick, game pad, satellite dish, scanner, or the like. These and other input devices are often connected to the processing unit through a user input interface that is coupled to the system bus, but may be connected by other interface and bus structures, such as a parallel port, game port or a universal serial bus (USB). A monitor or other type of display device is also connected to the system bus via an interface, such as a video interface. In addition to the monitor, the computer system may also include other peripheral output devices such as speakers and printers may be connected through an output peripheral interface.

The computing devices utilized in the present invention may operate in a networked environment using logical connections to one or more remote computers that typically includes many or all of the elements described above. When used in a LAN networking environment, the computing device may be connected to the LAN through a network interface or adapter. When used in a WAN networking environment, the computing device typically includes a modem or other means for establishing communications over the WAN, such as the Internet. The modem, which may be internal or external, may be connected to the system bus via the user input interface, or other appropriate mechanism. In a networked environment, program modules may be stored in the remote memory storage device. Although the components of the computing device are not shown, those of ordinary skill in the art will appreciate that such components and the interconnection are well known.

III. System and Method of the Invention

As illustrated in FIG. 2, in embodiments of the invention, the filtering system 100 includes a primary filter 110, one or more secondary filters 130 and 140, location filters 150, and column level filters 170. The primary filter 110 receives primary key information from the primary key generator 8, 10, 12 and makes an initial determination regarding whether an event is reportable.

The primary key generators 8, 10, 12 send records including patient information, diagnosing institution information, and event information to the filtering system 100. The patient information may include identifying information such as patient name, address, identifying number, sex, age, etc. The diagnosing institution information may include name, city, state, zip code, and hospital code. The event information depends upon the types of events detected. The types of biological event information that may be forwarded to the filtering system 100 may be of three basic types including: (1) test results; (2) clinical events; and (3) environmental events. Test results may include human results, animal results, environmental results or food industry results. Test results are likely to expose presence of a pathogen, presence of a test ordered, presence of chemicals, or exposure to ionizing radiation. Clinical events may include medical or surgical clinical orders, admissions, discharges, or complaints related to a syndrome, codified events, or death certificates. Environmental events may be based on environmental sensor results and may include presence of pathogens or chemicals.

The primary filter 110 determines if the forwarded records contain biological events that are of concern to any jurisdiction. The primary filter 110 considers the record forwarded without considering any demographics of the patient or of the reporting institution. The primary filter 110 only considers whether the specific type of event reported will be potentially interesting to any receiving entity. Based on information provided by each receiving entity, the primary filter 110 considers an event category, and filters out any events that do not fall within a category defined as reportable by any of the receiving institutions. Thus, the primary filter eliminates categories of events that are irrelevant to all receiving institutions.

The primary filter 110 associates a code with each reportable event. For instance, assuming that a record forwarded by a primary key generator includes an instance of a pathogen, the primary filter 110 identifies the recorded event as a pathogen presence, and determines if the presence of the particular pathogen is classified as a reportable event by any receiving jurisdiction. Each receiving entity has an assigned organizational identifier. If the event is reportable, the primary filter 110 creates a record for each receiving entity, identified by the assigned organizational code for that receiving entity, and attaches a reportable event identifying code to the record. Accordingly, a single pathogen occurrence may generate three separate records for three separate organizations when passing through the primary filter 110. Each record, if it passes through subsequent filters, would ultimately be passed to a distinct receiving organization as identified by the attached organizational code. The primary filter 110 forwards all of the create records along with the attached codes to the secondary filters 130, 140.

The secondary filters 130 and 140 of the filtering system 100 include additional results definitions for filtering test results. Although two secondary filters are shown, a single secondary filter or additional secondary filters may be utilized to implement the technique of the invention. Continuing with the pathogen example, the secondary filter 130 may include groups of categories for pathogens. For example, the pathogen information may include a pathogen description, a site description, susceptibility information, and a test result source. The secondary filters 130, 140 may "AND" the results from the primary filter with specific site information for each organization identified by the organizational codes. The secondary filters 130, 140 handle records similarly to the primary filters by creating an additional record for each secondary filter. The secondary filters 130, 140 determine if an AND or an OR should be applied between records created by the primary filtering process and process each record to determine if it meets the secondary filtering criteria. The system retains a distinct record for each organization having results that satisfy the secondary filtering criteria.

For example, perhaps a receiving entity identified by organizational code 157 is concerned only with the presence of the detected pathogen in the blood and not with the presence of the pathogen in the ear, nose, or throat. Accordingly, the secondary filters retain the records created showing the presence of the pathogen in the blood and not those showing the presence of the pathogen in the ear, nose, or throat. Other secondary filters may be provided for considering patient criteria such as age bracket, sex, or drug resistance. Each record passed to the secondary filters is evaluated based on the limitations provided by each identified receiving organization.

The secondary filters may include results definitions that include combinations of laboratory results to indicate whether a present pathogen is drawn from a particular site and/or whether antibiotic resistance is present. Results definitions may further include presence of additional pathogens or comorbidities such as those that create opportunistic infections for HIV. The results definitions may further include the presence of clinical conditions such as loss of vision, cancer, and wasting syndrome. Results definitions may further classify results based on a result level or on patient demographics such as pregnancy, death, or age at time of result. Further, the presence of an ordered test may be reportable. For instance, performance of an HIV test may be reportable regardless of test results. Additionally, a system performing a test or a type of test performed may be reportable. For instance, *e. coli* may be reportable if it was found with a human micro test, but not from a veterinary office test or a general laboratory test. Results definitions may further include presence of chemicals that could be indicated by environmental exposure record or a priority list of hazardous substances as defined by ATSDR (Agency for Toxic Substances and Disease Registry). Other results definitions may include presence of clinical conditions such as respiratory or neurological illness. These results definitions may be combined using "AND" and "OR" logical operators within the secondary filters 130 and 140 to operate on the records created by the primary filter 110.

Clinical event definitions may also be used in a similar manner to operate on the records created by the primary filter 110. The clinical event definitions may include patient demographics information as set forth above. The clinical event definitions may further include presence of predefined symptoms or syndromes such as gastrointestinal and respiratory illness and presence of specified clinically coded events, such as accident/injuries, poisoning, vaccinations, metabolic screens, birth defects, animal bites, occupational diseases, therapies, or chronic conditions such as asthma, diabetes, or cancer. Again, the presence of an ordered test may be reportable regardless of the test result. Clinical event definitions may further include cause of death, such as drowning or HIV.

Environmental event definitions may also be used within the secondary filters 130, 140 and in the same manner operate on the set of records provided by the primary filter 110. The environmental event definitions may include presence of pathogens such as bacteria or their toxins, viruses, fungi, protozoa, helminthes, or ectoparasites in the air or water supply. The environmental event definitions may also include such factors as location, level of result, and presence of a chemical.

The secondary filters 130, 140 pass the created records to the location filter 150. The location filter 150 may consider the demographic details of the residence of the patient, location of the patient's employer, school district of the patient, institution reporting the event, diagnosing institution, environmental sample location, or of the clinical event location. For instance, the location filter 150 may be configured to consider the city, state, zip code, county, or climate zone of the diagnosing institution. Furthermore, in some instances, a location where a test was performed may be different from a location where the test was ordered, or a location from where a sample was drawn. Receiving organizations may limit their data to reports from specific institutions or to institutions located within a predetermined geographic area. For instance, a health department in Philadelphia, PA may be interested in all reports from the mid-Atlantic region of the United States, but may have no interest in reported events in California. Health departments may supply various criteria for including reports from health care institutions. For example, these criteria may include any combinations of zip code, county, city, state, region, division, country, council district, census tract, congressional district, or estimated metropolitan area. Furthermore, the criteria may include geographic boundaries such as climate zone, geographic code, and address. Receiving institutions may "AND" and "OR" combinations of these criteria to incorporate in the location filter 150 in order to limit the results passed to requesting institutions.

The location filter 150 passes the filtered records to column level filters 170. The column level filters 170 consider the characteristics of the patient. The patient characteristics may include a patient name, social security number, phone number, address, school district, employment location, or encounter number. The column level filters 170 may further limit the number of data elements related to a set of results based upon the residence of the patient or other factors. The column level filters 170 filter received records by blinding or masking results within a record or set of results that are reportable to a receiving entity. The blinding or masking may occur due to limited rights of the receiving entity or due to the receiving entity's lack of interest in viewing particular results within a record.

Furthermore, the system described above may be a two-tier system. The filters may initially process a record at a group or institutional level. After the record has passed through the filters at a group level and a record has been created for each receiving institution, the record passed to an institution can then pass through the filters at an individual level for each applicable group. Further filtering processes will be required to identify subject matter uniquely relevant to individuals within a group. Typically, individuals associated with a receiving institution will receive a more limited set of records than the institution receives.

In additional embodiments of the invention, receiving institutions are able to identify alertable events. In this instance, specific events will generate an alert to the institution.

Figure 3:
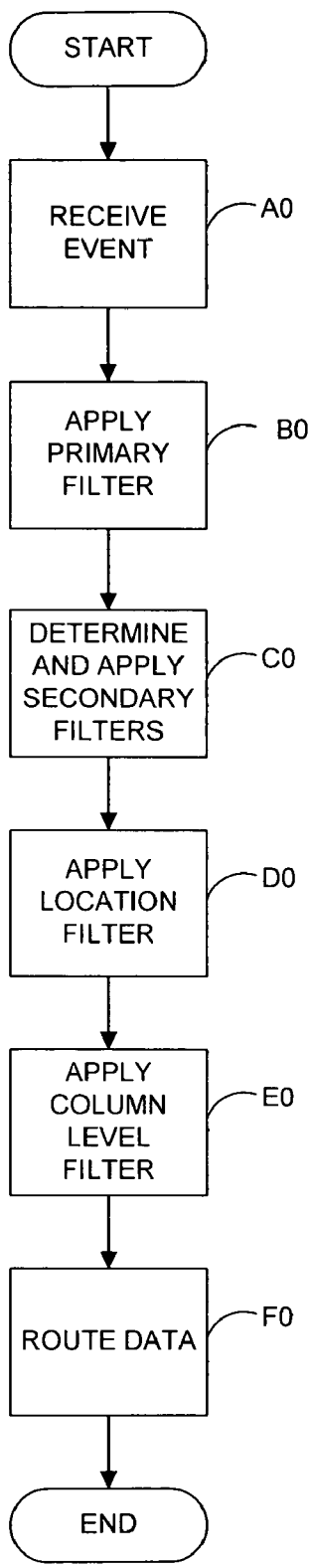
FIG. 3 is a flow chart illustrating a procedure for filtering and reporting events in accordance with an embodiment of the invention.

FIG. 3 is a flowchart illustrating a method in accordance with an embodiment of the invention. In step A0, the filtering system 100 receives an event from the primary key filter. In step B0, the filtering system 100 applies the primary filter 110 and creates records for each potential receiving institution.

The filtering system 100 determines and applies secondary filters in step C0. The system applies location filters in step D0. In step E0, the system applies column level filters, and in step F0, the system routes the remaining data to the appropriate results databases. As set forth above, this system is a two-tiered system and accordingly, the steps shown in FIG. 3 may be performed at an organizational level and subsequently at a user level.

Figure 4:
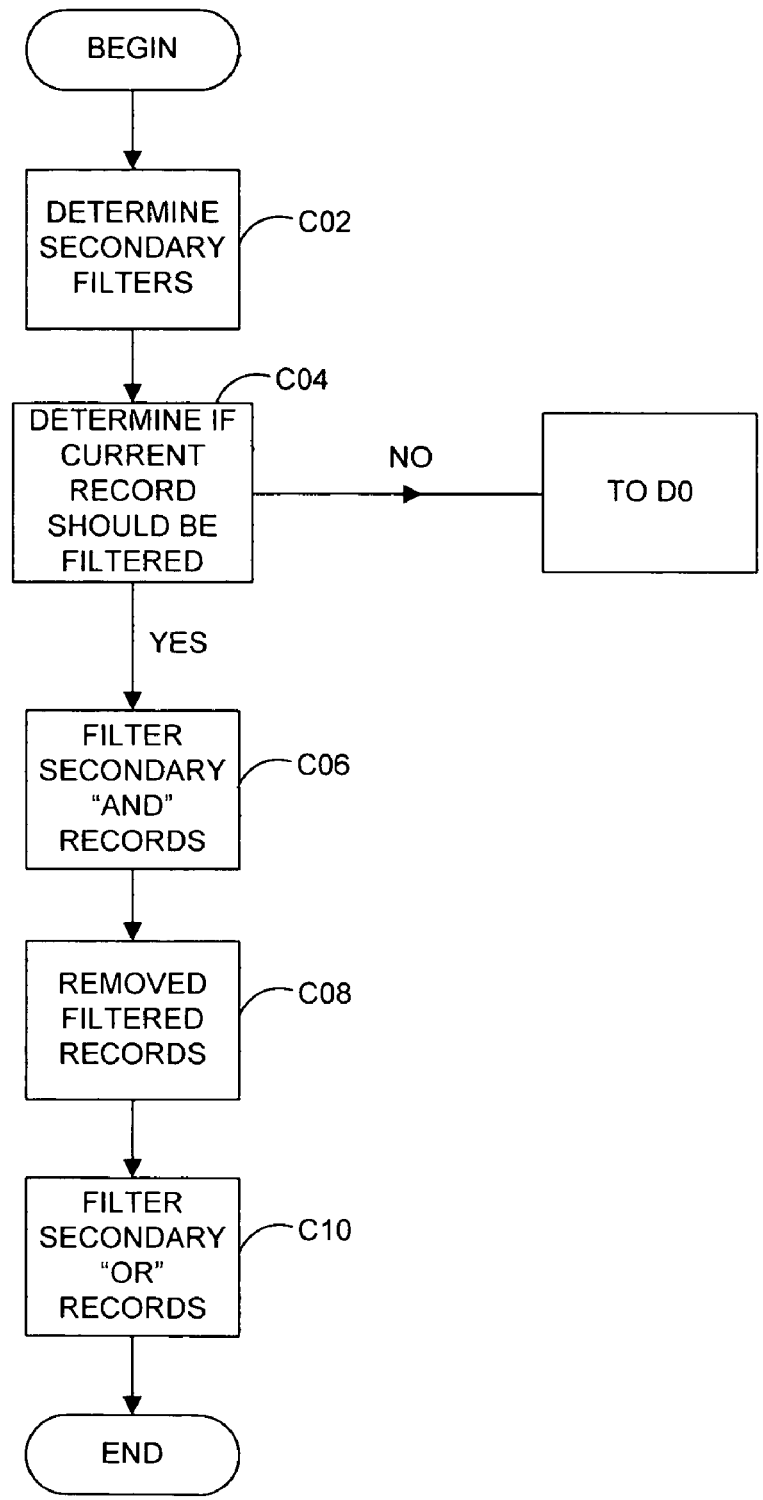
FIG. 4 is a flow chart illustrating a secondary filtering procedure in accordance with an embodiment of the invention.

FIG. 4 illustrates a procedure for applying the secondary filters as set forth in procedure C0. In step C02, the system determines the secondary filters. In step C04, the system determines if the current record should be filtered. In some instances, a clinical event will not have an applicable secondary filter. For instance, a health department may want to have every instance of an anthrax event reported, without regard for any additional characteristics of the anthrax diagnosis. If the current record will not be filtered based on secondary factors, the system proceeds to the location filters in step D0. If the record will be filtered, the system filters secondary "AND" records in step C06 and removes the filtered records in step C08. In step C10, the system filters secondary "OR" records. As set forth above in the description of the secondary filters, in steps C08 and C10, the system creates records for each AND and OR combination applied by the secondary filter to the record created by the primary filter. The system retains a distinct record for each organization having results that satisfy the secondary filtering criteria.

Figure 5:
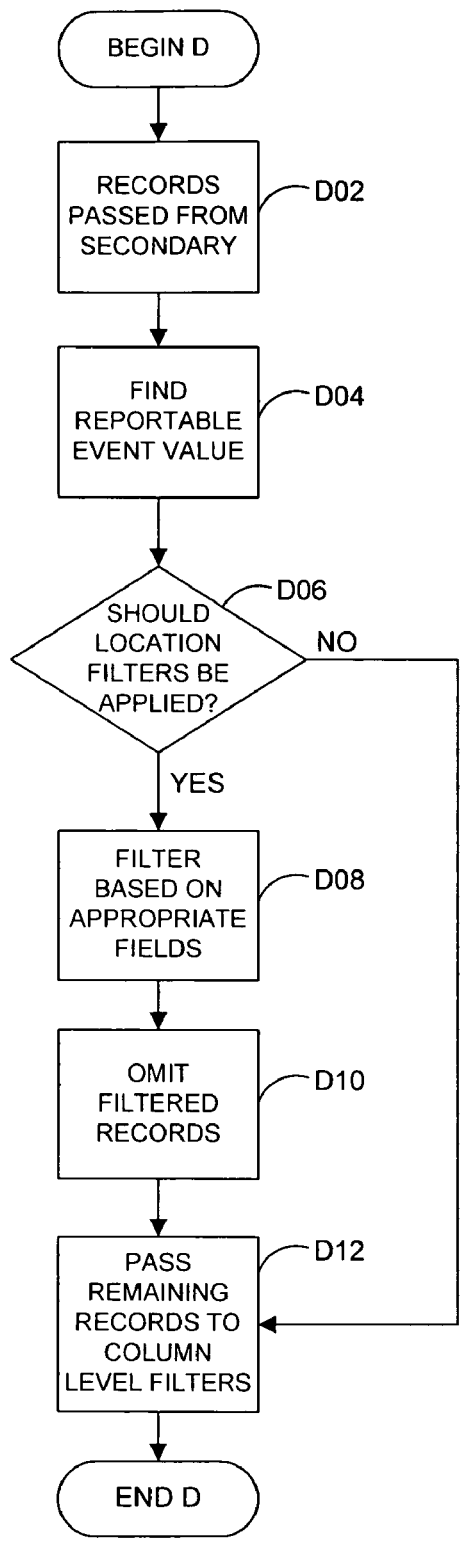
FIG. 5 is a flow chart illustrating a technique for applying location filters in accordance with an embodiment of the invention.

FIG. 5 illustrates the procedure for applying the location filters 150. In step D02, the location filters 150 receive the records passed from the secondary filters 130, 140. In step D04, the location filters 150 find the reportable event value. Based on the identification of the reportable event, the system determines in step D06 whether the location filters 150 should be applied. If application of the location filters is found to be appropriate in step D06, the location filters 150 filter based on appropriate fields in step D08. In step D10, the location filters omit the filtered records. In step D12, the location filters 150 pass the remaining records to the column level filters 170. If in step D06, application of the location filters is not appropriate, the system passes the remaining records directly to the column level filters 170 in step D12 without location filtering.

Figure 6:
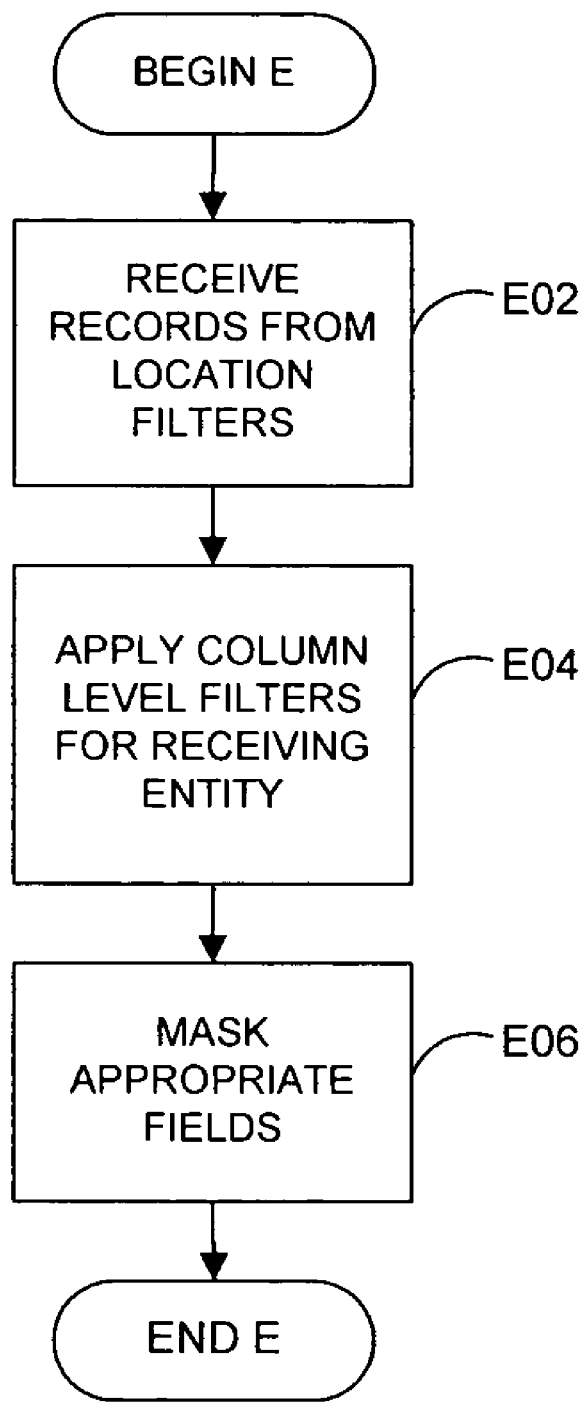
FIG. 6 is a flow chart illustrating a technique for applying a column level filter in accordance with an embodiment of the invention

FIG. 6 illustrates system procedures after location filtering. In step E02, column level filters 170 receive records from the location filters 150. In step E04 the system applies any existing column level filters 170 for the entity receiving each record. In step E06, the column level filters 170 mask or blind selected fields within a record. For instance, an agency or individuals within a particular agency may have limited viewing rights or may not want to receive some types of data within a record. The resultant records may show null values in the masked fields or may employ any number of techniques for masking the appropriate information. As shown in FIG. 3, in step F0, the filtered records are routed to each receiving entity after passing through the column level filters 170. As set forth above, the method of the invention may be a two-tier method in order to create a set of records for an agency and for selected individuals within an agency.

While particular embodiments of the invention have been illustrated and described in detail herein, it should be understood that various changes and modifications might be made to the invention without departing from the scope and intent of the invention. The embodiments described herein are intended in all respects to be illustrative rather than restrictive. Alternate embodiments will become apparent to those skilled in the art to which the present invention pertains without departing from its scope.

From the foregoing it will be seen that this invention is one well adapted to attain all the ends and objects set forth above, together with other advantages, which are obvious and inherent to the system and method. It will be understood that certain features and sub-combinations are of utility and may be employed without reference to other features and sub-combinations. This is contemplated and within the scope of the appended claims.

What is claimed is:

1. A computer-storage medium having embodied thereon computer-executable instructions, that, when executed by a computer, cause the computer to perform a method for processing a biological event record received from at least one reporting organization and delivering information from the biological event record to at least one receiving organization, the method comprising:

receiving a biological event record from each of a plurality of separate reporting organizations, each biological event record comprising information associated with a biological event, wherein the separate reporting organizations are not associated with each other;

identifying an event category corresponding to each biological event;

determining that at least one receiving organization from among a listing of a plurality of receiving organizations has requested notification of biological events corresponding to an identified event category, the listing further comprising reportable events corresponding to each of the plurality of receiving organizations, wherein the listing is stored in a database accessible by the computer;

creating a record for the at least one receiving organization;

filtering the created record based on criteria provided by the at least one receiving organization;

filtering the created record using a location filter for applying demographic criteria definitions for a biological event to the created record;

applying a secondary filter that applies results definitions to the created record; and providing the filtered record to at least one receiving individual at the at least one receiving organization such that the filtered record can be displayed to the at least one receiving individual.

2. The computer-storage medium of claim 1, further comprising applying demographic criteria to the created record, the demographic criteria including geographic restrictions for a record receiving organization.

3. The computer-storage medium of claim 1, further comprising implementing a patient characteristic filter for applying demographic criteria definitions related to a patient identified in the created record.

4. The computer-storage medium of claim 3, further comprising implementing the demographic criteria definitions to limit a patient residence to one of a specific zip code, a specific city, and a specific state.

5. The computer-storage medium of claim 1, further comprising applying a secondary filter that applies clinical event definitions to the created record.

6. The computer-storage medium of claim 1, further comprising applying a secondary filter that applies environmental event definitions to the created record.

7. The computer-storage medium of claim 1, further comprising performing the filtering step for a receiving organization and subsequently performing the filtering step for the at least one individual within the receiving organization, wherein the filtering step masks data fields within the created record.

8. A computer-storage medium having embodied thereon computer-executable instructions, that, when executed by a computer, cause the computer to perform a method for processing biological event records received from a plurality of reporting organizations and delivering information from the biological event record to a plurality of receiving organizations, the method comprising:

receiving a biological event record from one of the plurality of separate reporting organizations, the biological event record comprising information associated with a biological event;

identifying an event category corresponding to the biological event;

determining that a first receiving organization from among a listing of a plurality of receiving organizations has requested notification of biological events corresponding to the identified event category, the listing further comprising reportable events corresponding to each of the plurality of receiving organizations;

determining that a second receiving organization from among the listing of the plurality of receiving organizations has requested notification of biological events corresponding to the identified event category;

creating a first record for the first receiving organization;

creating a second record for the second receiving organization;

filtering the first created record based on a first set of criteria provided by the first receiving organization;

filtering the second created record based on a second set of criteria provided by the second receiving organization, wherein the first set of criteria is not the same as the second set of criteria;

creating a third record using the filtered first created record;

creating a fourth record using the filtered second created record;

applying a first secondary filter that applies a first set of results definitions to the third record, thereby creating a first result record, wherein the first set of results definitions are established by the first receiving organization;

applying a second secondary filter that applies a second set of results definitions to the fourth record, thereby creating a second result record, wherein the second set of results definitions are established by the second receiving organization;

delivering the first result record to a first results database, wherein the first results database is maintained by the first receiving organization; and delivering the second result record to a second results database, wherein the second results database is maintained by the second receiving organization.

9. A computing device for processing a biological event record received from at least one reporting organization and delivering information from the biological event record to at least one receiving organization, the device comprising:

a system bus;

a system memory coupled to the system bus, wherein the system memory includes computer storage media having computer-executable instructions embodied thereon; and a processing unit coupled to the system memory via the system bus, wherein the processing unit executes the computer-executable instructions to cause the computing device to perform the following steps:

(1) receiving a biological event record from each of a plurality of separate reporting organizations, each biological event record comprising information associated with a biological event, wherein the separate reporting organizations are not associated with each other;

(2) identifying an event category corresponding to each biological event;

(3) determining that at least one receiving organization from among a listing of a plurality of receiving organizations has requested notification of biological events corresponding to an identified event category, the listing further comprising reportable events corresponding to each of the plurality of receiving organizations;

(4) creating a record for the at least one receiving organization;

(5) filtering the created record based on criteria provided by the at least one receiving organization;

(6) filtering the created record using a location filter for applying demographic criteria definitions for a biological event to the created record;

(7) applying a secondary filter that applies results definitions to the created record; and (8) providing the filtered record to at least one results database at the at least one receiving organization such that the filtered record can be displayed to at least one receiving individual.

10. The device of claim 9, further comprising:

(9) applying demographic criteria to the created record, the demographic criteria including geographic restrictions for a record receiving organization.

11. The device of claim 10, further comprising:

(10) implementing a patient characteristic filter for applying demographic criteria definitions related to a patient identified in the created record.

12. The device of claim 10, wherein applying the demographic criteria to the created record includes implementing the demographic criteria definitions to limit a patient residence to one of a specific zip code, a specific city, and a specific state.

13. A computer-implemented method for using a computing device to process a biological event record received from at least one reporting organization and delivering information from the biological event record to at least one receiving organization, the method comprising:

receiving, at the computer, a biological event record from each of a plurality of separate reporting organizations, each biological event record comprising information associated with a biological event, wherein the separate reporting organizations are not associated with each other;

identifying, using the computer, an event category corresponding to each biological event;

determining, using the computer, that at least one receiving organization from among a listing of a plurality of receiving organizations has requested notification of biological events corresponding to an identified event category, the listing further comprising reportable events corresponding to each of the plurality of receiving organizations;

creating, using the computer, a record for the at least one receiving organization;

filtering, using the computer, the created record based on criteria provided by the at least one receiving organization;

filtering, using the computer, the created record using a location filter for applying demographic criteria definitions for a biological event to the created record;

applying, using the computer, a secondary filter that applies results definitions to the created record; and providing, using the computer, the filtered record to at least one receiving individual at the at least one receiving organization such that the filtered record can be displayed to the at least one receiving individual.

14. The computer-implemented method of claim 13, further comprising applying demographic criteria to the created record, the demographic criteria including geographic restrictions for a record receiving organization.

15. The computer-implemented method of claim 13, further comprising implementing a patient characteristic filter for applying demographic criteria definitions related to a patient identified in the created record.

16. The computer-implemented method of claim 15, further comprising implementing the demographic criteria definitions to limit a patient residence to one of a specific zip code, a specific city, and a specific state.

17. The computer-implemented method of claim 13, further comprising applying a secondary filter that applies clinical event definitions to the created record.

18. The computer-implemented method of claim 13, further comprising applying a secondary filter that applies environmental event definitions to the created record.

19. The computer-implemented method of claim 13, further comprising performing the filtering step for a receiving organization and subsequently performing the filtering step for the at least one individual within the receiving organization, wherein the filtering step masks data fields within the created record.

* * * * *